United States Patent
Spenciner et al.

(10) Patent No.: US 10,751,041 B2
(45) Date of Patent: *Aug. 25, 2020

(54) SURGICAL FILAMENT ASSEMBLIES

(71) Applicant: Medos International Sàrl, Le Locle (CH)

(72) Inventors: David B. Spenciner, North Attleboro, MA (US); Benjamin Chan, Naples, FL (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 250 days.

This patent is subject to a terminal disclaimer.

(21) Appl. No.: 15/840,106

(22) Filed: Dec. 13, 2017

(65) Prior Publication Data

US 2018/0098763 A1    Apr. 12, 2018

Related U.S. Application Data

(60) Continuation of application No. 14/334,844, filed on Jul. 18, 2014, now Pat. No. 9,872,678, which is a
(Continued)

(51) Int. Cl.
*A61B 17/04* (2006.01)

(52) U.S. Cl.
CPC .. *A61B 17/0401* (2013.01); *A61B 2017/0412* (2013.01); *A61B 2017/0422* (2013.01);
(Continued)

(58) Field of Classification Search
CPC ............ A61B 17/0401; A61B 17/0642; A61B 2017/0427; A61B 2017/0446;
(Continued)

(56) References Cited

U.S. PATENT DOCUMENTS 2,566,625 A   9/1951   Nagelmann
2,600,395 A   6/1952   Domoj et al.
(Continued)

FOREIGN PATENT DOCUMENTS

AU           724861 B2   10/2000
AU       2008229746 A1   10/2008
(Continued)

OTHER PUBLICATIONS

Google dictionary definition of the term "Tube" retrieved Nov. 24, 2019 (Year: 2019).*
(Continued)

*Primary Examiner* — Ryan J. Severson

(57) ABSTRACT

A suture anchor, and a surgical filament assembly using same, capable of being fixated in a hole formed in a bone of a patient. The suture anchor preferably includes an anchor body having a distal end, a proximal end, a passage extending from the proximal end toward the distal end, at least one feature disposed on the exterior of the anchor to engage bone, and a filament knot patency element disposed within the passage and defining a channel having a sufficient minimum cross-sectional area to allow movement of a portion of a surgical filament therethrough when a removable sliding knot is formed, using the surgical filament, about the filament knot patency element. The surgical filament assembly preferably includes a first filament having a sliding knot removably positioned about the knot patency element, with a shortening limb and a tightening limb each extending from the sliding knot. The sliding knot defines an adjustable capture loop having two legs extending proximally to a bight, one leg transitioning into the shortening limb and passing through the channel of the knot patency element, the shortening limb being accessible to enable a user to shorten the capture loop. The tightening limb enables the user to tighten the sliding knot against an object extend-
(Continued)

ing through the capture loop to secure the object to the anchor.

12 Claims, 6 Drawing Sheets

Related U.S. Application Data division of application No. 13/435,790, filed on Mar. 30, 2012, now Pat. No. 8,790,370.

(52) U.S. Cl.
CPC ............ *A61B 2017/0424* (2013.01); *A61B 2017/0427* (2013.01); *A61B 2017/0445* (2013.01); *A61B 2017/0448* (2013.01); *A61B 2017/0451* (2013.01)

(58) Field of Classification Search
CPC .... A61B 2017/0425; A61B 2017/0448; A61B 2017/045; A61B 2017/0456; A61B 2017/0458; A61B 2017/0459; A61B 2017/0462; A61B 2017/0461; A61B 2017/0412; A61B 2017/0414; A61B 2017/0445; A61B 2017/0451; A61F 2/0811
USPC ........ 606/139, 148–150, 187, 228–232, 300, 606/301, 304; 623/13.11–1.2
See application file for complete search history.

(56) References Cited

U.S. PATENT DOCUMENTS

| | | |
|---|---|---|
| 2,697,624 A | 12/1954 | Thomas et al. |
| 2,758,858 A | 8/1956 | Smith |
| 2,992,029 A | 7/1961 | Russell |
| 3,106,417 A | 10/1963 | Clow |
| 3,131,957 A | 5/1964 | Musto |
| 3,177,021 A | 4/1965 | Benham |
| 3,402,957 A | 9/1968 | Peterson |
| 3,521,918 A | 7/1970 | Hammond |
| 3,565,077 A | 2/1971 | Glick |
| 3,580,256 A | 5/1971 | Wilkinson et al. |
| 3,712,651 A | 1/1973 | Shockley |
| 3,752,516 A | 8/1973 | Mumma |
| 3,873,140 A | 3/1975 | Bloch |
| 4,029,346 A | 6/1977 | Browning |
| 4,036,101 A | 7/1977 | Burnett |
| 4,038,988 A | 8/1977 | Perisse |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,186,921 A | 2/1980 | Fox |
| 4,205,399 A | 6/1980 | Shalaby et al. |
| 4,208,511 A | 6/1980 | Shalaby et al. |
| 4,319,428 A | 3/1982 | Fox |
| 4,403,797 A | 9/1983 | Ragland, Jr. |
| 4,510,934 A | 4/1985 | Batra |
| 4,572,554 A | 2/1986 | Janssen et al. |
| 4,792,336 A | 12/1988 | Hlavacek et al. |
| 4,870,957 A | 10/1989 | Goble et al. |
| 4,946,377 A | 8/1990 | Kovach |
| 4,962,929 A | 10/1990 | Melton, Jr. |
| 4,987,665 A | 1/1991 | Dumican et al. |
| 5,062,344 A | 11/1991 | Gerker |
| 5,098,137 A | 3/1992 | Wardall |
| 5,144,961 A | 9/1992 | Chen et al. |
| 5,156,616 A | 10/1992 | Meadows et al. |
| 5,178,629 A | 1/1993 | Kammerer |
| 5,217,495 A | 6/1993 | Kaplan et al. |
| 5,250,053 A | 10/1993 | Snyder |
| 5,250,054 A | 10/1993 | Li |
| 5,259,846 A | 11/1993 | Granger et al. |
| 5,263,984 A | 11/1993 | Li et al. |
| 5,279,311 A | 1/1994 | Snyder |
| 5,282,809 A | 2/1994 | Kammerer et al. |
| 5,284,485 A | 2/1994 | Kammerer et al. |
| 5,312,423 A | 5/1994 | Rosenbluth et al. |
| 5,318,575 A | 6/1994 | Chesterfield et al. |
| 5,320,629 A | 6/1994 | Noda et al. |
| 5,376,118 A | 12/1994 | Kaplan et al. |
| 5,391,176 A | 2/1995 | de la Torre |
| 5,395,382 A | 3/1995 | DiGiovanni et al. |
| 5,405,352 A | 4/1995 | Weston |
| 5,450,860 A | 9/1995 | O'Connor |
| 5,454,820 A | 10/1995 | Kammerer et al. |
| 5,456,722 A | 10/1995 | McLeod et al. |
| 5,464,427 A | 11/1995 | Curtis et al. |
| 5,464,929 A | 11/1995 | Bezwada et al. |
| 5,472,446 A | 12/1995 | de la Torre |
| 5,527,323 A | 6/1996 | Jervis et al. |
| 5,534,011 A | 7/1996 | Greene, Jr. et al. |
| 5,540,703 A | 7/1996 | Barker, Jr. et al. |
| 5,549,618 A | 8/1996 | Fleenor et al. |
| 5,562,684 A | 10/1996 | Kammerer |
| 5,569,306 A | 10/1996 | Thal |
| 5,571,139 A * | 11/1996 | Jenkins, Jr. ........ A61B 17/0401 606/232 |
| 5,573,286 A | 11/1996 | Rogozinski |
| 5,591,207 A | 1/1997 | Coleman |
| 5,593,189 A | 1/1997 | Little |
| 5,595,751 A | 1/1997 | Bezwada et al. |
| 5,597,579 A | 1/1997 | Bezwada et al. |
| 5,607,687 A | 3/1997 | Bezwada et al. |
| 5,618,552 A | 4/1997 | Bezwada et al. |
| 5,620,698 A | 4/1997 | Bezwada et al. |
| 5,628,756 A | 5/1997 | Barker |
| 5,645,850 A | 7/1997 | Bezwada et al. |
| 5,647,616 A | 7/1997 | Hamilton |
| 5,647,874 A | 7/1997 | Hayhurst |
| 5,648,088 A | 7/1997 | Bezwada et al. |
| 5,667,528 A | 9/1997 | Colligan |
| 5,683,417 A | 11/1997 | Cooper |
| 5,683,419 A | 11/1997 | Thal |
| 5,685,037 A | 11/1997 | Fitzner et al. |
| 5,698,213 A | 12/1997 | Jamiolkowski et al. |
| 5,700,583 A | 12/1997 | Jamiolkowski et al. |
| 5,702,397 A | 12/1997 | Goble et al. |
| 5,709,708 A | 1/1998 | Thal |
| 5,716,368 A | 2/1998 | de la Torre et al. |
| 5,725,556 A | 3/1998 | Moser et al. |
| 5,728,109 A | 3/1998 | Schulze et al. |
| 5,741,332 A | 4/1998 | Schmitt |
| 5,749,898 A | 5/1998 | Schulze et al. |
| 5,782,864 A | 7/1998 | Lizardi |
| 5,814,069 A | 9/1998 | Schulze et al. |
| 5,859,150 A | 1/1999 | Jamiolkowski et al. |
| 5,899,920 A | 5/1999 | DeSatnick et al. |
| 5,941,900 A | 8/1999 | Bonutti |
| 5,964,783 A | 10/1999 | Grafton et al. |
| 5,971,447 A | 10/1999 | Steck, III |
| 5,989,252 A | 11/1999 | Fumex |
| 6,024,758 A | 2/2000 | Thal |
| 6,045,574 A | 4/2000 | Thal |
| 6,143,017 A | 11/2000 | Thal |
| 6,221,084 B1 | 4/2001 | Fleenor |
| 6,267,766 B1 | 7/2001 | Burkhart |
| 6,296,659 B1 | 10/2001 | Foerster |
| 6,319,271 B1 | 11/2001 | Schwartz et al. |
| 6,322,112 B1 | 11/2001 | Duncan |
| 6,517,578 B2 | 2/2003 | Hein |
| 6,527,794 B1 | 3/2003 | McDevitt et al. |
| 6,527,795 B1 | 3/2003 | Lizardi |
| 6,540,750 B2 | 4/2003 | Burkhart |
| 6,547,807 B2 | 4/2003 | Chan et al. |
| 6,596,015 B1 | 7/2003 | Pitt et al. |
| 6,641,596 B1 | 11/2003 | Lizardi |
| 6,641,597 B2 | 11/2003 | Burkhart et al. |
| 6,652,563 B2 | 11/2003 | Dreyfuss |
| 6,660,023 B2 | 12/2003 | McDevitt et al. |
| 6,689,154 B2 | 2/2004 | Bartlett |

(56) References Cited

U.S. PATENT DOCUMENTS

| | | |
|---|---|---|
| 6,716,234 B2 | 4/2004 | Grafton et al. |
| 6,767,037 B2 | 7/2004 | Wenstrom, Jr. |
| 6,818,010 B2 | 11/2004 | Eichhorn et al. |
| 6,887,259 B2 | 5/2005 | Lizardi |
| 6,923,824 B2 | 8/2005 | Morgan et al. |
| 6,994,719 B2 | 2/2006 | Grafton |
| 7,029,490 B2 | 4/2006 | Grafton et al. |
| 7,048,754 B2 | 5/2006 | Martin et al. |
| 7,081,126 B2 | 7/2006 | McDevitt et al. |
| 7,217,279 B2 | 5/2007 | Reese |
| 7,226,469 B2 | 6/2007 | Benavitz et al. |
| 7,235,090 B2 | 6/2007 | Buckman et al. |
| 7,285,124 B2 | 10/2007 | Foerster |
| 7,309,337 B2 | 12/2007 | Colleran et al. |
| 7,338,502 B2 | 3/2008 | Rosenblatt |
| 7,381,213 B2 | 6/2008 | Lizardi |
| 7,390,332 B2 | 6/2008 | Selvitelli et al. |
| 7,455,684 B2 | 11/2008 | Gradel et al. |
| 7,582,105 B2 | 9/2009 | Kolster |
| 7,601,165 B2 | 10/2009 | Stone |
| 7,651,509 B2 | 1/2010 | Bojarski et al. |
| 7,654,321 B2 | 2/2010 | Zazovsky et al. |
| 7,658,750 B2 | 2/2010 | Li |
| 7,658,751 B2 | 2/2010 | Stone et al. |
| 7,682,374 B2 | 3/2010 | Foerster et al. |
| 7,695,495 B2 | 4/2010 | Dreyfuss |
| 7,703,372 B1 | 4/2010 | Shakespeare |
| 7,803,173 B2 | 9/2010 | Burkhart et al. |
| 7,875,043 B1 | 1/2011 | Ashby et al. |
| 7,883,528 B2 | 2/2011 | Grafton et al. |
| 7,883,529 B2 | 2/2011 | Sinnott et al. |
| 7,905,903 B2 | 3/2011 | Stone et al. |
| 7,905,904 B2 | 3/2011 | Stone et al. |
| 7,959,650 B2 | 6/2011 | Kaiser et al. |
| 7,981,140 B2 | 7/2011 | Burkhart |
| 8,012,171 B2 | 9/2011 | Schmieding |
| 8,088,130 B2 | 1/2012 | Kaiser et al. |
| 8,088,146 B2 | 1/2012 | Wert et al. |
| 8,114,128 B2 | 2/2012 | Cauldwell et al. |
| 8,118,836 B2 | 2/2012 | Denham et al. |
| 8,137,382 B2 | 3/2012 | Denham et al. |
| 8,231,653 B2 | 7/2012 | Dreyfuss |
| 8,231,654 B2 | 7/2012 | Kaiser et al. |
| 8,419,769 B2 | 4/2013 | Thal |
| 8,545,535 B2 | 10/2013 | Hirotsuka et al. |
| 8,608,758 B2 | 12/2013 | Singhatat et al. |
| 8,790,369 B2 | 7/2014 | Orphanos et al. |
| 8,790,370 B2 | 7/2014 | Spenciner et al. |
| 8,814,905 B2 | 8/2014 | Sengun et al. |
| 8,821,543 B2 | 9/2014 | Hernandez et al. |
| 8,821,544 B2 | 9/2014 | Sengun et al. |
| 8,821,545 B2 | 9/2014 | Sengun |
| 8,894,684 B2 | 11/2014 | Sengun |
| 8,974,495 B2 | 3/2015 | Hernandez et al. |
| 9,017,381 B2 | 4/2015 | Kaiser et al. |
| 9,034,013 B2 | 5/2015 | Sengun |
| 9,060,763 B2 | 6/2015 | Sengun |
| 9,060,764 B2 | 6/2015 | Sengun |
| 9,095,331 B2 | 8/2015 | Hernandez et al. |
| 9,179,908 B2 | 11/2015 | Sengun |
| 9,192,373 B2 | 11/2015 | Sengun |
| 9,198,653 B2 | 12/2015 | Sengun et al. |
| 9,271,716 B2 | 3/2016 | Sengun |
| 9,345,468 B2 | 5/2016 | Sengun et al. |
| 9,345,567 B2 | 5/2016 | Sengun |
| 9,532,778 B2 | 1/2017 | Sengun et al. |
| 9,737,293 B2 | 8/2017 | Sengun et al. |
| 9,757,116 B2 | 9/2017 | Sengun |
| 9,763,655 B2 | 9/2017 | Sengun |
| 9,795,373 B2 | 10/2017 | Sengun |
| 9,833,229 B2 | 12/2017 | Hernandez et al. |
| 9,872,678 B2 * | 1/2018 | Spenciner ......... A61B 17/0401 |
| 9,895,145 B2 | 2/2018 | Sengun et al. |
| 10,258,321 B2 | 4/2019 | Sengun |
| 10,271,833 B2 | 4/2019 | Sengun |
| 10,292,695 B2 | 5/2019 | Sengun et al. |
| 10,524,777 B2 | 1/2020 | Sengun |
| 2002/0019649 A1 | 2/2002 | Sikora et al. |
| 2002/0029066 A1 | 3/2002 | Foerster |
| 2003/0004545 A1 | 1/2003 | Burkhart et al. |
| 2003/0050667 A1 | 3/2003 | Grafton et al. |
| 2003/0120309 A1 | 6/2003 | Colleran et al. |
| 2003/0130695 A1 | 7/2003 | McDevitt et al. |
| 2003/0229362 A1 | 12/2003 | Chan et al. |
| 2004/0093031 A1 | 5/2004 | Burkhart et al. |
| 2004/0098050 A1 | 5/2004 | Foerster et al. |
| 2004/0153074 A1 | 8/2004 | Bojarski et al. |
| 2004/0172062 A1 | 9/2004 | Burkhart |
| 2004/0236373 A1 | 11/2004 | Anspach |
| 2005/0033363 A1 | 2/2005 | Bojarski et al. |
| 2005/0119696 A1 | 6/2005 | Walters et al. |
| 2005/0137624 A1 | 6/2005 | Fallman |
| 2005/0187577 A1 | 8/2005 | Selvitelli et al. |
| 2005/0251208 A1 | 11/2005 | Elmer et al. |
| 2006/0106423 A1 | 5/2006 | Weisel et al. |
| 2006/0178680 A1 | 8/2006 | Nelson et al. |
| 2006/0178702 A1 | 8/2006 | Pierce et al. |
| 2006/0293710 A1 | 12/2006 | Foerster et al. |
| 2007/0027476 A1 | 2/2007 | Harris et al. |
| 2007/0032792 A1 | 2/2007 | Collin et al. |
| 2007/0060922 A1 | 3/2007 | Dreyfuss |
| 2007/0083236 A1 | 4/2007 | Sikora et al. |
| 2007/0135843 A1 | 6/2007 | Burkhart |
| 2007/0150003 A1 | 6/2007 | Dreyfuss et al. |
| 2007/0156148 A1 | 7/2007 | Fanton et al. |
| 2007/0156149 A1 | 7/2007 | Fanton et al. |
| 2007/0156150 A1 | 7/2007 | Fanton et al. |
| 2007/0156176 A1* | 7/2007 | Fanton ............... A61B 17/0401 606/232 |
| 2007/0219557 A1 | 9/2007 | Bourque et al. |
| 2007/0219558 A1 | 9/2007 | Deutsch |
| 2007/0225719 A1 | 9/2007 | Stone et al. |
| 2007/0239209 A1 | 10/2007 | Fallman |
| 2008/0009901 A1 | 1/2008 | Redmond et al. |
| 2008/0009904 A1 | 1/2008 | Bourque et al. |
| 2008/0027446 A1 | 1/2008 | Stone et al. |
| 2008/0065114 A1 | 3/2008 | Stone et al. |
| 2008/0077182 A1 | 3/2008 | Geissler et al. |
| 2008/0091237 A1 | 4/2008 | Schwartz et al. |
| 2008/0103528 A1 | 5/2008 | Zirps et al. |
| 2008/0140092 A1 | 6/2008 | Stone et al. |
| 2008/0147063 A1 | 6/2008 | Cauldwell et al. |
| 2008/0188893 A1 | 8/2008 | Selvitelli et al. |
| 2008/0195205 A1 | 8/2008 | Schwartz |
| 2008/0208265 A1 | 8/2008 | Frazier et al. |
| 2008/0228265 A1 | 9/2008 | Spence et al. |
| 2008/0255613 A1 | 10/2008 | Kaiser et al. |
| 2008/0275469 A1 | 11/2008 | Fanton et al. |
| 2008/0312689 A1 | 12/2008 | Denham et al. |
| 2009/0023984 A1 | 1/2009 | Stokes et al. |
| 2009/0036905 A1 | 2/2009 | Schmieding |
| 2009/0043317 A1 | 2/2009 | Cavanaugh et al. |
| 2009/0054928 A1 | 2/2009 | Denham et al. |
| 2009/0062850 A1 | 3/2009 | Ken |
| 2009/0062854 A1 | 3/2009 | Kaiser et al. |
| 2009/0082805 A1 | 3/2009 | Kaiser et al. |
| 2009/0082807 A1 | 3/2009 | Miller et al. |
| 2009/0088798 A1 | 4/2009 | Snyder et al. |
| 2009/0099598 A1 | 4/2009 | McDevitt et al. |
| 2009/0138042 A1 | 5/2009 | Thal |
| 2009/0234387 A1 | 9/2009 | Miller et al. |
| 2009/0281568 A1 | 11/2009 | Cendan et al. |
| 2009/0281581 A1 | 11/2009 | Berg |
| 2009/0287246 A1 | 11/2009 | Cauldwell et al. |
| 2009/0306711 A1 | 12/2009 | Stone et al. |
| 2009/0312776 A1 | 12/2009 | Kaiser |
| 2009/0312794 A1 | 12/2009 | Nason et al. |
| 2009/0318958 A1 | 12/2009 | Ochiai |
| 2010/0004683 A1 | 1/2010 | Hoof et al. |
| 2010/0016892 A1* | 1/2010 | Kaiser ............... A61B 17/0401 606/232 |
| 2010/0094425 A1 | 4/2010 | Bentley et al. |
| 2010/0162882 A1 | 7/2010 | Shakespeare |
| 2010/0204730 A1 | 8/2010 | Maiorino et al. |

(56) References Cited

U.S. PATENT DOCUMENTS

| | | |
|---|---|---|
| 2010/0249809 A1 | 9/2010 | Singhatat et al. |
| 2010/0249834 A1 | 9/2010 | Dreyfuss |
| 2010/0256677 A1 | 10/2010 | Albertorio et al. |
| 2010/0292732 A1 | 11/2010 | Hirotsuka et al. |
| 2010/0292792 A1 | 11/2010 | Stone et al. |
| 2011/0022083 A1 | 1/2011 | DiMatteo et al. |
| 2011/0022084 A1 | 1/2011 | Sengun et al. |
| 2011/0077667 A1 | 3/2011 | Singhatat et al. |
| 2011/0098727 A1 | 4/2011 | Kaiser et al. |
| 2011/0152928 A1 | 6/2011 | Colleran et al. |
| 2011/0190815 A1 | 8/2011 | Saliman |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0238111 A1 | 9/2011 | Frank |
| 2011/0264140 A1 | 10/2011 | Lizardi et al. |
| 2011/0264141 A1 | 10/2011 | Denham et al. |
| 2011/0270278 A1 | 11/2011 | Overes et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0101523 A1 | 4/2012 | Wert et al. |
| 2012/0101524 A1 | 4/2012 | Bennett |
| 2012/0130423 A1 | 5/2012 | Sengun et al. |
| 2012/0130424 A1 | 5/2012 | Sengun et al. |
| 2012/0150223 A1 | 6/2012 | Manos et al. |
| 2012/0165864 A1 | 6/2012 | Hernandez et al. |
| 2012/0179199 A1 | 7/2012 | Hernandez et al. |
| 2012/0253389 A1 | 10/2012 | Sengun et al. |
| 2012/0253390 A1 | 10/2012 | Sengun |
| 2012/0296375 A1 | 11/2012 | Thal |
| 2013/0110165 A1 | 5/2013 | Burkhart et al. |
| 2013/0158598 A1 | 6/2013 | Lizardi |
| 2013/0253581 A1 | 9/2013 | Robison |
| 2013/0261664 A1 | 10/2013 | Spenciner et al. |
| 2013/0296895 A1 | 11/2013 | Sengun |
| 2013/0296896 A1 | 11/2013 | Sengun |
| 2013/0296931 A1 | 11/2013 | Sengun |
| 2013/0296934 A1 | 11/2013 | Sengun |
| 2014/0081324 A1 | 3/2014 | Sengun |
| 2014/0107701 A1 | 4/2014 | Lizardi et al. |
| 2014/0188163 A1 | 7/2014 | Sengun |
| 2014/0188164 A1 | 7/2014 | Sengun |
| 2014/0277132 A1 | 9/2014 | Sengun et al. |
| 2014/0330312 A1 | 11/2014 | Spenciner et al. |
| 2014/0343606 A1 | 11/2014 | Hernandez et al. |
| 2014/0343607 A1 | 11/2014 | Sengun et al. |
| 2015/0012038 A1 | 1/2015 | Sengun et al. |
| 2015/0025572 A1 | 1/2015 | Sengun |
| 2015/0045832 A1 | 2/2015 | Sengun |
| 2015/0238183 A1 | 8/2015 | Sengun |
| 2015/0245832 A1 | 9/2015 | Sengun |
| 2015/0297214 A1 | 10/2015 | Hernandez et al. |
| 2015/0313587 A1 | 11/2015 | Lizardi et al. |
| 2016/0128687 A1 | 5/2016 | Sengun |
| 2016/0278761 A1 | 9/2016 | Sengun et al. |
| 2016/0296222 A1 | 10/2016 | Sengun |
| 2017/0000479 A1 | 1/2017 | Sengun et al. |
| 2017/0303913 A1 | 10/2017 | Sengun et al. |
| 2017/0360428 A1 | 12/2017 | Sengun |
| 2017/0367690 A1 | 12/2017 | Sengun |
| 2018/0042600 A1 | 2/2018 | Hernandez et al. |
| 2018/0140292 A1 | 5/2018 | Sengun et al. |
| 2019/0216457 A1 | 7/2019 | Sengun |

FOREIGN PATENT DOCUMENTS

| | | |
|---|---|---|
| CA | 2772500 A1 | 9/2013 |
| CN | 2719234 Y | 8/2005 |
| CN | 101252887 A | 8/2008 |
| CN | 101442944 A | 5/2009 |
| CN | 101961256 A | 2/2011 |
| CN | 102113901 A | 7/2011 |
| EP | 0 870 471 A1 | 10/1998 |
| EP | 1 199 035 A1 | 4/2002 |
| EP | 1 707 127 A1 | 10/2006 |
| EP | 2 277 457 A1 | 1/2011 |
| EP | 2 455 003 A2 | 5/2012 |
| EP | 2 572 650 A1 | 3/2013 |
| JP | 2000-512193 A | 9/2000 |
| JP | 2008-543509 A | 12/2008 |
| WO | 95/019139 A1 | 7/1995 |
| WO | 97/017901 A1 | 5/1997 |
| WO | 98/011825 A1 | 3/1998 |
| WO | 98/042261 A1 | 10/1998 |
| WO | 01/06933 A2 | 2/2001 |
| WO | 03/022161 A1 | 3/2003 |
| WO | 2007/002561 A1 | 1/2007 |
| WO | 2007/005394 A1 | 1/2007 |
| WO | 2007/078281 A2 | 7/2007 |
| WO | 2007/109769 A1 | 9/2007 |

OTHER PUBLICATIONS

\*\*[No Author Listed] Arthroscopic Knot Tying Manual 2005. DePuy Mitek. 27 pages.

\*\*[No Author Listed] Gryphon Brochure. DePuy Mitek. 2 pages (undated).

\*\*[No Author Listed] Versalok Anchor. Brochure. DePuy Mitek, a Johnson & Johnson company, 92 pages, 2007.

\*\*Allcock, The Encyclopedia of Polymer Science, vol. 13, pp. 31-41, Wiley Intersciences, John Wiley & Sons, 1988.

\*\*Chinese Office Action for Application No. 201310163420.7, dated May 5, 2016 (21 pages).

\*\*Chinese Office Action for Application No. 201310163700.8 dated Jun. 3, 2016 (14 pages).

\*\*Chinese Office Action for Application No. 201310429109.2 dated Oct. 24, 2016 (13 pages).

\*\*Chinese Office Action for Application No. 201310741440.8, dated Jan. 26, 2017 (12 pages).

\*\*Cohn et al., Biodegradable PEO/PLA block copolymers. J Biomed Mater Res. Nov. 1988;22(11):993-1009.

\*\*Cohn et al., Polym Preprint. 1989;30(1):498.

\*\*Dahl et al., Biomechanical characteristics of 9 arthroscopic knots. Arthroscopy. Jun. 2010;26(6):813-8.

\*\*EP Search Report for Application No. 11190157.5 dated Feb. 27, 2012. (8 pages).

\*\*Extended European Search Report for Application No. 11190157.5 dated Jul. 6, 2012. (10 pages).

\*\*EP Search Report for Application No. 11190159.1 dated Feb. 21, 2012. (8 pages).

\*\*Extended European Search Report for Application No. 11190159.1 dated Jul. 6, 2012. (11 pages).

\*\*Extended European Search Report for Application No. 11195100.0 dated Oct. 17, 2012. (7 pages).

\*\*Extended European Search Report for Application No. 13166905.3 dated Aug. 13, 2013 (9 Pages).

\*\*Extended European Search Report for Application No. 13166907.9, dated Aug. 1, 2013 (6 pages).

\*\*Extended European Search Report for Application No. 13166908.7, dated Aug. 23, 2013 (8 pages).

\*\*Extended European Search Report for Application No. 13185425.9 dated Dec. 16, 2013 (9 Pages).

\*\*Extended European Search Report for Application No. 13199724.9 dated Apr. 4, 2014 (6 Pages).

Extended European Search Report for Application No. 16205548.7, dated Dec. 22, 2017 (11 pages).

\*\*Heller, Handbook of Biodegradable Polymers, edited by Domb, et al., Hardwood Academic Press, pp. 99-118 (1997).

\*\*International Search Report for Application No. PCT/US2011/067119, dated Jun. 4, 2012. (6 pages).

\*\*Japanese Office Action for Application No. 2011-281088, dated Nov. 10, 2015 (4 pages).

\*\*Japanese Office Action for Application No. 2013-097645, dated May 9, 2017 (6 pages).

Japanese Office Action for Application No. 2013-268840, dated Sep. 26, 2017 (5 pages).

(56) References Cited

OTHER PUBLICATIONS

**Kemnitzer et al., Handbook of biodegradable Polymers. Eds. Domb et al. Hardwood Acad. Press. 1997;251-72.
**Vandorpe et al., Handbook of Biodegradable Polymers, edited by Domb, et al., Hardwood Acad. Press, pp. 161-182 (1997).
U.S. Appl. No. 16/363,421, filed Mar. 25, 2019, Surgical Constructs and Methods for Securing Tissue.
U.S. Appl. No. 12/977,146, filed Dec. 23, 2010, Adjustable Anchor Systems and Methods.
U.S. Appl. No. 12/977,154, filed Dec. 23, 2010, Surgical Filament Snare Assemblies.
U.S. Appl. No. 13/218,810, filed Aug. 26, 2011, Surgical Filament Snare Assemblies.
U.S. Appl. No. 13/336,151, filed Dec. 23, 2011, Adjustable Anchor Systems and Methods.
U.S. Appl. No. 13/435,790, filed Mar. 30, 2012, Surgical Filament Assemblies.
U.S. Appl. No. 13/435,834, filed Mar. 30, 2012, Surgical Filament Snare Assemblies.
U.S. Appl. No. 13/435,846, filed Mar. 30, 2012, Surgical Filament Snare Assemblies.
U.S. Appl. No. 13/465,288, filed May 7, 2012, Systems, Devices, and Methods for Securing Tissue.
U.S. Appl. No. 13/465,299, filed May 7, 2012, Systems, Devices, and Methods for Securing Tissue.
U.S. Appl. No. 13/465,362, filed May 7, 2012, Systems, Devices, and Methods for Securing Tissue Using a Suture Having One or More Protrusions.
U.S. Appl. No. 13/465,376, filed May 7, 2012, Systems, Devices, and Methods for Securing Tissue Using Snare Assemblies and Soft Anchors.
U.S. Appl. No. 13/623,429, filed Sep. 20, 2012, Systems, Devices, and Methods for Securing Tissue Using Hard Anchors.
U.S. Appl. No. 13/728,044, filed Dec. 27, 2012, Surgical Constructs and Methods for Securing Tissue.
U.S. Appl. No. 14/145,486, filed Dec. 31, 2013, Surgical Constructs With Collapsing Suture Loop and Methods for Securing Tissue.
U.S. Appl. No. 14/145,501, filed Dec. 31, 2013, Surgical Constructs and Methods for Securing Tissue.
U.S. Appl. No. 14/334,844, filed Jul. 18, 2014, Surgical Filament Assemblies.
U.S. Appl. No. 14/448,812, filed Jul. 31, 2014, Adjustable Anchor Systems and Methods.
U.S. Appl. No. 14/448,827, filed Jul. 31, 2014, Surgical Filament Snare Assemblies.
U.S. Appl. No. 14/448,847, filed Jul. 31, 2014, Surgical Filament Snare Assemblies.
U.S. Appl. No. 14/448,852, filed Jul. 31, 2014, Surgical Filament Snare Assemblies.
U.S. Appl. No. 14/522,562, filed Oct. 23, 2014, Systems, Devices, and Methods for Securing Tissue Using a Suture Having One or More Protrusions.
U.S. Appl. No. 14/711,959, filed May 14, 2015, Systems, Devices, and Methods for Securing Tissue Using a Suture Having One or More Protrusions.
U.S. Appl. No. 14/713,566, filed May 15, 2015, Systems, Devices, and Methods for Securing Tissue.
U.S. Appl. No. 14/754,773, filed Jun. 30, 2015, Adjustable Anchor Systems and Methods.
U.S. Appl. No. 15/001,513, filed Jan. 20, 2016, Surgical Constructs and Methods for Securing Tissue.
U.S. Appl. No. 15/143,496, filed Apr. 29, 2016, Systems, Devices, and Methods for Securing Tissue Using Snare Assemblies and Soft Anchors.
U.S. Appl. No. 15/143,502, filed Apr. 29, 2016, Surgical Filament Snare Assemblies.
U.S. Appl. No. 15/264,645, filed Sep. 14, 2016, Surgical Filament Snare Assemblies.
U.S. Appl. No. 15/648,068, filed Jul. 12, 2017, Surgical Constructs With Collapsing Suture Loop and Methods for Securing Tissue.
U.S. Appl. No. 15/692,885, filed Aug. 31, 2017, Systems, Devices, and Methods for Securing Tissue Using Hard Anchors.
U.S. Appl. No. 15/700,901, filed Sep. 11, 2017, Systems, Devices, and Methods for Securing Tissue.
U.S. Appl. No. 15/794,625, filed Oct. 27, 2017, Adjustable Anchor Systems and Methods.
U.S. Appl. No. 15/874,063, filed Jan. 18, 2018, Surgical Filament Snare Assemblies.
U.S. Appl. No. 16/703,421, filed Dec. 4, 2019, Systems, Devices, and Methods For Securing Tissue.
Indian First Examination Report for Application No. 3243/DEL/2011, dated Dec. 30, 2019 (6 pages).

* cited by examiner

SURGICAL FILAMENT ASSEMBLIES

This application is a continuation of U.S. patent application Ser. No. 14/334,844, filed on Jul. 18, 2014, and entitled "Surgical Filament Assemblies," which is a divisional of U.S. application Ser. No. 13/435,790, filed on Mar. 30, 2012, entitled "Surgical Filament Assemblies," and which issued as U.S. Pat. No. 8,790,370 on Jul. 29, 2014, each of which is hereby incorporated by reference in its entirety.

BACKGROUND OF THE INVENTION

Field of the Invention

The invention relates to anchors and filament assemblies for securing tissue to bone and more particularly to adjustable tensioning of tissue independent of anchor fixation.

Description of the Related Art

A common injury, especially among athletes, is the complete or partial detachment of tendons, ligaments or other soft tissues from bone. Tissue detachment may occur during a fall, by overexertion, or for a variety of other reasons. Surgical intervention is often needed, particularly when tissue is completely detached from its associated bone. Currently available devices for tissue attachment include screws, staples, suture anchors and tacks.

Arthroscopic knot tying is commonly practiced in shoulder rotator cuff and instability procedures. Typically, an anchor loaded with suture is attached to bone first. The suture is normally slidably attached to the anchor through an eyelet or around a post, such that a single length of suture has two free limbs. One limb of the suture is passed through soft tissue to be repaired such as a tendon or labrum. The two ends of the suture are then tied to each other, thereby capturing the soft tissue in a loop with the anchor. Upon tightening the loop, the soft tissue is approximated to the bone via the anchor.

Surgeons typically tie the suture ends by first placing a surgical sliding knot such as the Tennessee Slider or Duncan Knot. After tightening the loop, a number of additional half hitches or other knots are tied. The additional knots are needed because a conventional sliding knot does not provide the necessary protection against loosening or slippage, especially when tension is placed primarily on the limbs of the loop. Generally accepted practice is to follow the sliding knot with at least three reversed half hitches on alternating posts of the suture.

Before one or more half hitches or other knots can be added to the sliding knot, however, there exists a potential for the sliding knot to slip, that is, for the loop to enlarge as the tissue places tension on the loop. This has been referred to as "loop security" and can reportedly occur even in the hands of very experienced surgeons. Sometimes, even fully-tied knots may slip. Further, the overall size of a conventional knot can be obstructive or intrusive, especially in tight joints, which may damage cartilage or other tissue by abrasion with the knot.

Suture anchor systems with sliding and locking knots for repairing torn or damaged tissue include U.S. Pat. No. 6,767,037 by Wenstrom, Jr. Other suture anchor systems suited especially for meniscal repair are disclosed in U.S. Pat. No. 7,390,332 by Selvitelli et al. and are utilized in the OmniSpan™ meniscal repair system commercially available from DePuy Mitek Inc., 325 Paramount Drive, Raynham, Mass. 02767.

One of the present inventors is also an inventor of U.S. application Ser. No. 13/218,810 entitled "Surgical Filament Snare Assemblies", filed 26 Aug. 2011, which claims priority to U.S. Provisional Application No. 61/416,562 filed 23 Nov. 2010 and to U.S. patent application Ser. No. 12/977,146 (Hernandez et al.) and Ser. No. 12/977,154 (Sengun et al.) filed 23 Dec. 2010.

There are a number of suture implant systems which proclaim to be "knotless", that is, to not require a surgeon to tie a knot during surgery. Many such systems control tension on tissue by the depth to which an anchor is driven into bone. U.S. Pat. Nos. 5,782,864 and 7,381,213 by Lizardi disclose certain types of suture anchors which capture a fixed-length loop of suture. Adjustable loop knotless anchor assemblies utilizing an anchor element inserted into a sleeve are described by Thal in U.S. Pat. Nos. 5,569,306 and 6,045,574 and in U.S. Patent Application Publication No. 2009/0138042. Other allegedly knotless anchoring devices are disclosed in U.S. Pat. No. 7,682,374 by Foerster et al. and in U.S. Patent Application Publication No. 2008/0009904 by Bourque et al. Yet other systems having clamps or other locking mechanisms include U.S. Pat. No. 5,702,397 by Goble et al. and U.S. Patent Application Publication No. 2008/0091237 by Schwartz et al.

It is therefore desirable to have robust yet adjustable fixation of tissue while minimizing both the number and size of knots to be tied by a surgeon, especially during arthroscopic repair procedures.

SUMMARY OF THE INVENTION

An object of the present invention is to meet or exceed the tissue tension control and holding power of currently available suture anchor assemblies for tissue repair procedures while reducing the number of half hitches or other knots to be tied by a surgeon.

Another object of the present invention is to maintain a tied but not fully tightened knot within the suture anchor until deployment is desired.

A still further object is to simplify the overall knot tying process for the surgeon.

Yet another object of the present invention is to enable incremental tensioning of tissue after anchor fixation.

This invention features a suture anchor for use as a surgical filament assembly capable of being fixated in a hole formed in a bone of a patient. In some embodiments, the suture anchor includes an anchor body having a distal end, a proximal end, a passage extending from the proximal end toward the distal end, at least one feature disposed on the exterior of the anchor to engage bone, and a filament knot patency element disposed within the passage and defining a channel having a sufficient size, that is, minimum cross-sectional area, to allow movement of a first portion of a surgical filament therethrough when a removable sliding knot is formed, using the surgical filament, about the filament knot patency element.

In one embodiment, the filament knot patency element includes a hollow, substantially cylindrical member defining the channel as an internal passageway through the member. In another embodiment, the knot patency element is a means for maintaining patency of the sliding knot until a user manipulates at least a second portion of the surgical filament to tighten the sliding knot and slidably remove the knot from the knot patency element. Preferably, the knot patency element is formed integrally with the anchor body as a substantially tubular member that extends proximally within the passage of the anchor body. The knot patency element may define at least one feature that alters the tendency of the slip knot to reside on the knot patency element, such as one or more of an outer surface that tapers in increasing cross-sectional area proximally to encourage knot removal, an outer surface that tapers in increasing cross-sectional area distally to retard knot removal, at least one rib or other type of projection, at least one depression or other type of indentation, texturing, and coatings that alter the coefficient of friction for at least a portion of the outer surface of the knot patency element.

This invention also features a surgical filament assembly including a first filament having a sliding knot removably positioned about the knot patency element, with a shortening limb and a tightening limb each extending from the sliding knot. The sliding knot defines an adjustable capture loop having two legs extending proximally to a bight, one leg transitioning into the shortening limb and passing through the channel of the knot patency element, the shortening limb being accessible to enable a user to shorten the capture loop. The tightening limb extends proximally, over at least an initial portion of its length, to enable the user to tighten the sliding knot against an object extending through the capture loop to secure the object to the anchor.

In some embodiments, the object is a second filament capable of being passed through tissue to be repaired and then passable through the capture loop to enable incremental tensioning of the tissue after the anchor is fixated in bone, the capture loop strangulating the second filament when tension is applied to at least the tightening limb of the first filament. In other embodiments, a portion of the shortening limb is passed through tissue and then through the capture loop. In certain embodiments, a mechanism locks the shortening limb in a desired position.

A suture anchor according to the present invention in one embodiment comprises an anchor body having a distal end and a proximal end. A suture construct couples to the anchor body, the suture construct comprising a length of suture having a knot. A knot patentcy element on the body is removably received within the knot and holds the knot in a first non-cinched configuration. The knot also has a second cinched configuration.

Preferably, the suture construct further includes a collapsing loop formed through the knot. Preferably, the collapsing loop comprises a shortening limb passing through the knot, the shortening limb being slidable through the knot when the knot is in the uncinched configuration. When the knot is in the cinched configuration, sliding of the shortening limb through the knot is inhibited by the knot. In one aspect of the invention, a tissue suture is received through the collapsing loop. The tissue suture passes through or around a tissue to attach the the tissue to the anchor. The tissue suture can comprise a fixed end of the knot.

Preferably, the knot patency element comprises a tube received within the knot and a tube cannulation through the tube. Preferably, the suture construct further comprises a collapsing loop formed through the knot and the collapsing loop comprises a shortening limb passing through the knot. The shortening limb is slidable through the tube cannulation and through the knot when the knot is in the uncinched configuration to collapse the collapsible loop. When the knot is in the cinched configuration sliding of the shortening limb through the knot is inhibited by the knot.

Preferably, the anchor body comprises a body cannulation therethrough from the proximal end to the distal end and the tube is disposed within this body cannulation. Preferably, the shortening end extends distally from the knot and exits the body cannulation at the body distal end. Preferably, the collapsing loop extends proximally out of the body cannulation at the body proximal end.

A feature can be provided to alters the tendency of the knot to stay on the patency element. For instance, the patency element can have a length and a free end which is removable from the knot and a change in circumference of the patency element along its length toward its free end could be provided to increase or decrease the tendency of the knot to slide off of the patency element.

A locking mechanism can be associated with the body for receiving the shortening limb so as to lock the shortening limb in a desired position.

This invention may be expressed as a method of surgically repairing tissue by selecting an anchor capable of being fixated in bone and having a filament knot patency element with a sliding knot in a first filament removably positioned about the knot patency element, the first filament having a shortening limb and a tightening limb each extending from the sliding knot. The sliding knot defines an adjustable capture loop having two legs extending proximally to a bight, one leg transitioning into the shortening limb and passing through the channel of the knot patency element. The shortening limb is accessible to enable a user to shorten the capture loop. At least a portion of an object is passed through a portion of the tissue and then passed through the capture loop. The anchor is fixated in bone. The tissue is then tensioned as desired and the tightening limb is manipulated so that the capture loop strangulates the object when tension is applied to at least the tightening limb to enable incremental tensioning of the tissue after the anchor is fixated.

In some embodiments, the shortening limb is manipulated to reduce the size of the capture loop as desired, preferably after the portion of the object is passed through the capture loop. In certain embodiments, the object is a second filament capable of being passed through tissue to be repaired and then passed through the capture loop to enable incremental tensioning of the tissue after the anchor is fixated in bone.

BRIEF DESCRIPTION OF THE DRAWINGS

In what follows, preferred embodiments of the invention are explained in more detail with reference to the drawings, in which.

DETAILED DESCRIPTION OF THE PRESENTLY PREFERRED EMBODIMENTS

This invention may be accomplished by a suture anchor, and a surgical filament assembly using same, capable of being fixated in a hole formed in a bone of a patient. The suture anchor preferably includes an anchor body having a distal end, a proximal end, a passage extending from the proximal end toward the distal end, at least one feature disposed on the exterior of the anchor to engage bone, and a filament knot patency element disposed within the passage, that is, disposed internally within the anchor body. The filament knot patency element defines a channel having a sufficient minimum cross-sectional area to allow movement of a portion of a surgical filament therethrough when a removable sliding knot is formed, using the surgical filament, about the filament knot patency element.

The surgical filament assembly preferably includes a first filament such as a suture having a sliding knot removably positioned about the knot patency element, with a shortening limb and a tightening limb each extending from the sliding knot. The sliding knot defines an adjustable capture loop having two legs extending proximally to a bight, one leg transitioning into the shortening limb and passing through the channel of the knot patency element, the shortening limb being accessible to enable a user to shorten the capture loop. The tightening limb extends proximally, over at least an initial portion of its length, to enable the user to tighten the sliding knot against an object extending through the capture loop to secure the object to the anchor.

Figure 1:
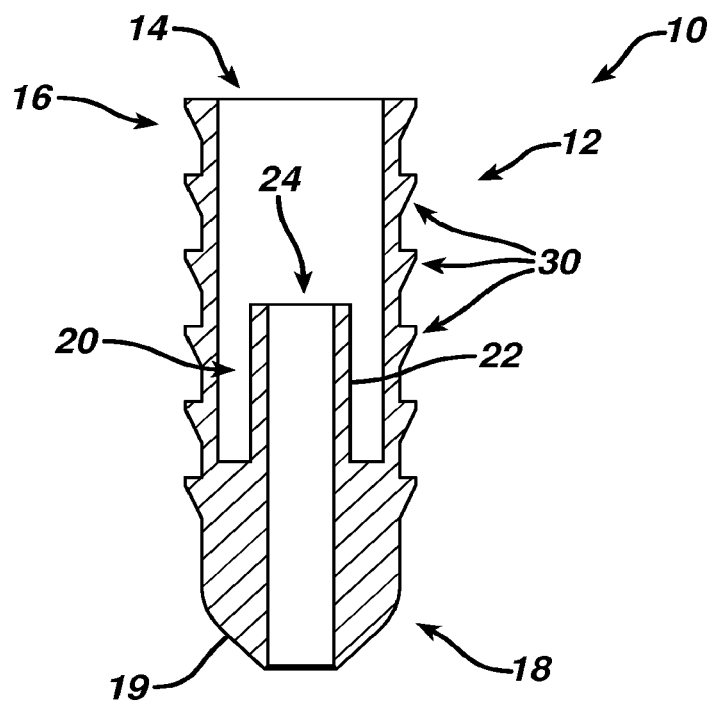
FIG. 1 is a schematic side cross-sectional view of a suture anchor according to the present invention having a filament knot patency element.

One construction of a suture anchor according to the present invention is shown in cross-section in FIG. 1 as suture anchor 10 having a substantially cylindrical anchor body 12 defining a central passage 14 extending from proximal end 16 toward distal end 18, which includes a sloped surface 19 to assist insertion into a hole formed in bone of a patient. In this construction, a filament knot patency element 20 is formed as an integral tube 22 within passage 14 and defines a passageway 24 as a channel extending to distal end 18. In this construction, passageway 24 may be interpreted as a distal extension of passage 14 to enable open communication between proximal end 16 and distal end 18, although open communication between ends 16 and 18 is not a limitation of the invention. The outer surface of tube 22 preferably is sufficiently smooth, that is, has a sufficiently low coefficient of friction, to enable a knot to slide along its surface as described in more detail below. A plurality of bone-engaging features 30, such as ribs or a helical thread, enhance fixation of anchor 10 after it is inserted into the hole in bone.

Figure 2:
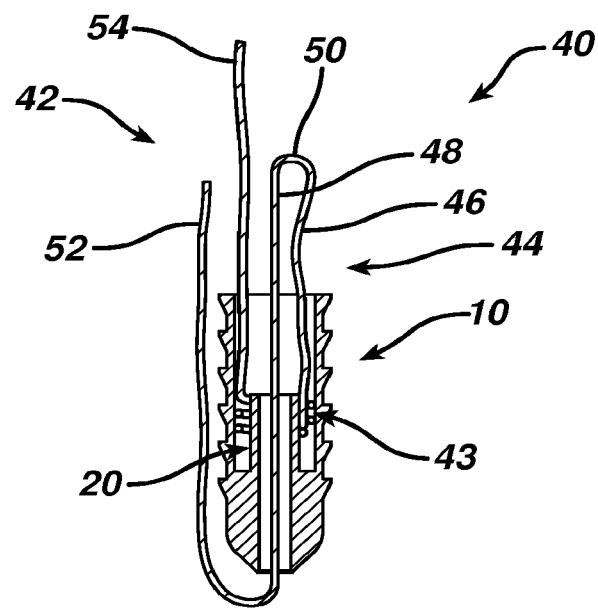
FIG. 2 is a view of FIG. 1 with a first filament having a sliding knot removably positioned about the knot patency element to form a surgical filament assembly with capture loop according to the present invention.

Anchor 10 is shown in FIG. 2 as part of surgical filament assembly 40 according to the present invention with filament 42. A removable slip knot 43 is tied about knot patency element 20 with a capture loop 44 having legs 46 and 48 extending proximally to a bight 50. Leg 48 transitions through slip knot 43 and knot patency element 20 to become shortening limb 52. The other free limb extending from slip knot 43 is a tightening limb 54.

Figure 3:
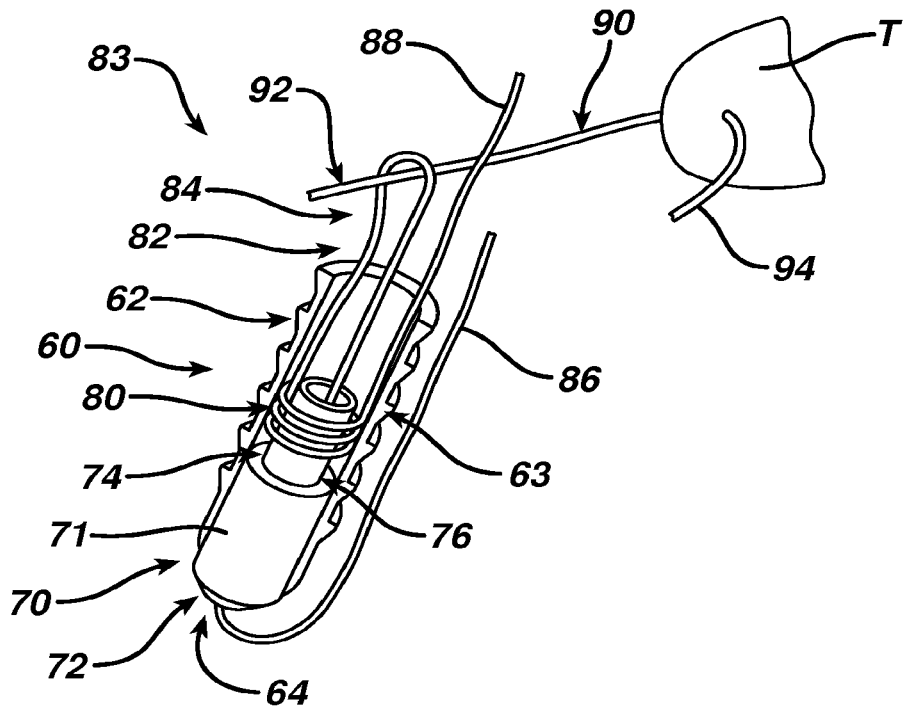
FIG. 3 is a schematic perspective, partial cross-sectional view similar to FIG. 2 showing a object passed through tissue and then through the capture loop of an alternative surgical filament assembly according to the present invention.

Another construction of a suture anchor according to the present invention is shown in FIG. 3 as suture anchor 60 having anchor body 62 formed as a hollow cylinder with outer surface 63 having one or more bone engagement features. Component 70 has a base 71 with a distal surface 72 which forms distal tip 64 of anchor 60. A tubular structure 74 extends proximally from base 71 to form knot patency element 76. A slip knot 80 of first filament 82 is tied about knot patency element 76, and is removable as described in more detail below, to establish surgical filament assembly 83 according to the present invention. Component 70 is formed from the same conventional material as anchor body 62 in some constructions and, in other constructions, is formed from a different material, preferably with a low coefficient of friction especially for tubular structure 74. In some constructions, tubular structure 74 has substantially parallel walls and, in other constructions, has one or more of the shapes and features described below in relation to FIGS. 11-14.

Capture loop 84 emerges proximally from anchor 60 and is shown with a first portion 92 of an object 90 passing through capture loop 84 after passing through tissue T. Another portion 94 of object 90, on the opposite side of tissue T, is also passed through capture loop 84 in some constructions, such as where object 90 is a second filament. In another construction, shortening limb 86 serves as the object 90; in other words, portion 94 is connected to shortening limb 86 in that construction and only a single limb of first filament 82 extends through capture loop 84. In all constructions, tightening limb 88 is accessible external to the anchor, either proximally or distally, as described in more detail below. Manipulating a portion of shortening limb 86, such as by pulling it away from anchor 60, will draw object portion 92 toward anchor 60 as capture loop 84 is reduced in size.

Figure 4:
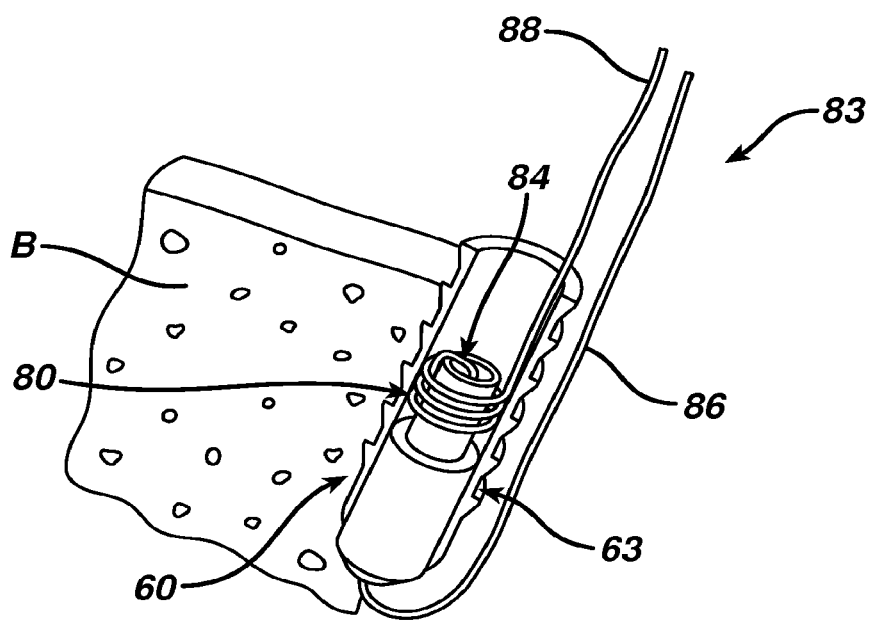
FIG. 4 shows the surgical filament assembly of FIG. 3 after the capture loop has been shortened and the suture anchor fixated in bone, without showing the object or tissue.

Anchor 60 is shown in FIG. 4 inserted into a hole in bone B, preferably after capture loop 84 has been drawn toward or within anchor 60 by manipulation of shortening limb 86. To allow partial insertion of the anchor 60 into the hole while still allowing manipulation of the tensioning limb 86 the suture can exit the anchor through a side window (not shown) preferably distal of the engagement features. After the loop 84 is adjusted as desired the anchor 60 would then be fully inserted to capture the limb 86. Object 90 and tissue T have been omitted from FIG. 4 for ease of illustration. In one construction, shortening limb 86 is locked in position by frictional engagement between outer surface 63 of anchor 60 and bone B. In other constructions, shortening limb 86 is held in position by a locking mechanism or other arrangement such as described in relation to FIGS. 15 and 16 below.

Suitable instruments for inserting anchors 10 and 60 into a hole drilled in bone include cannulated drivers such as described in Cauldwell et al. in U.S. Patent Application Publication No. 2008/0147063, incorporated herein by reference. In one construction, suture anchor 10, FIGS. 1 and 2, is similar to the cannulated suture anchor disclosed by Cauldwell et al. having a post-like suture-engaging member or other occluding element over which one or more sutures or suture limbs pass to serve as a restriction to proximal movement of the first filament. Because a post-like suture-engaging member enables a limb of the first filament to reverse direction and extend proximally, open communication with a distal end of the anchor is not required.

Figure 5:
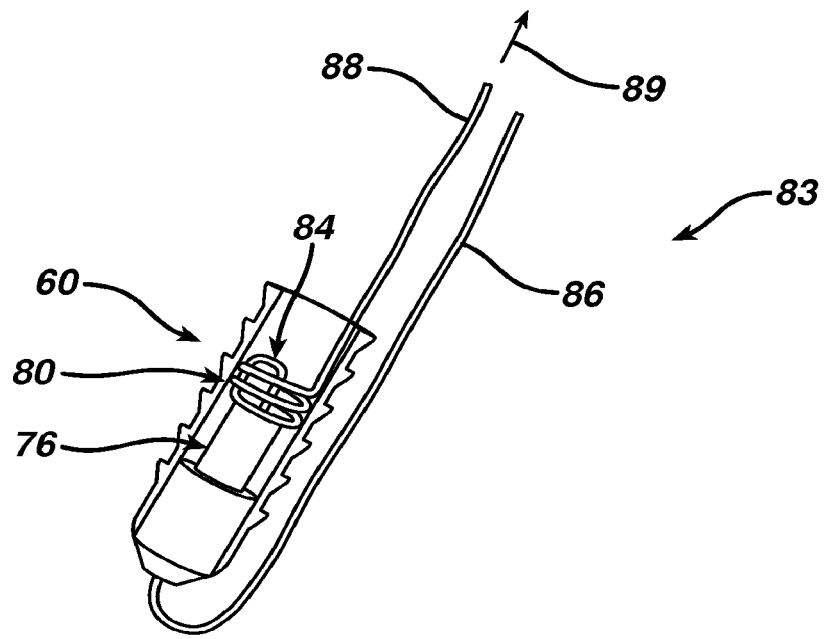
FIGS. 5 and 6 are sequential views of the filament assembly of FIG. 4 as the slip knot is tightened and removed from the knot patency element.
Figure 6:
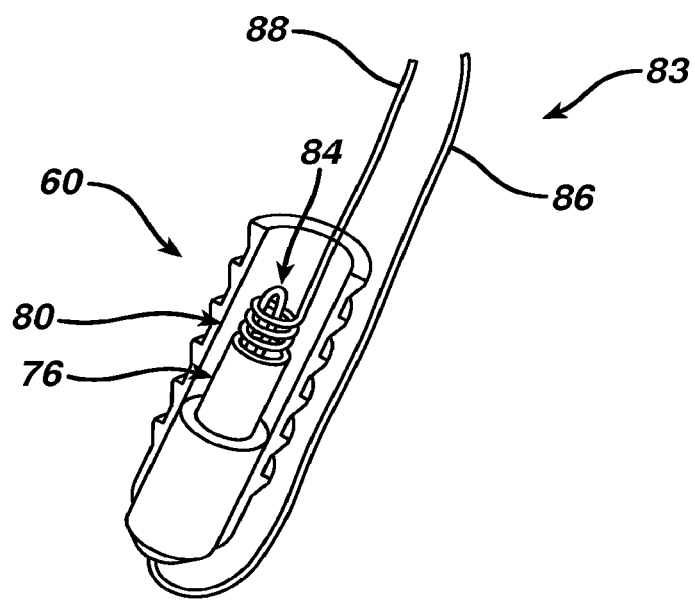

In one procedure according to the present invention, after the anchor 60 has been inserted into bone B, FIG. 4, a surgeon or other user places desired tension on limb 92 of object 90 and grasps tightening limb 88 to withdraw tightening limb away from anchor 60 as indicated by arrow 89, FIG. 5. This action tightens slip knot 80 and moves knot 80 proximally over knot patency element 76, as illustrated in FIG. 5, and then enables capture loop 84, FIG. 6, to strangulate one or more objects previously placed through capture loop 84. When tightening limb 88 is pulled sufficiently, the capture loop 84 may draw captured objects through the knot 80 to the other, distal side of knot 80. Further tensioning tightens the knot 80. When the one or more captured objects are pulled within knot 80, a surgeon or other user may feel a "flip" or "click" signifying that knot 80 has been sufficiently tightened.

The anchor 60 could also be used as the lateral anchor in a dual row rotator cuff procedure. It would receive a suture or sutures from one or more medial row anchors (not shown) through the capture loop 84 which would then be tightened to capture the suture from the medial row anchors. One or more knots could be placed into this suture to prevent it from slipping back through the capture loop 84.

Figure 7:
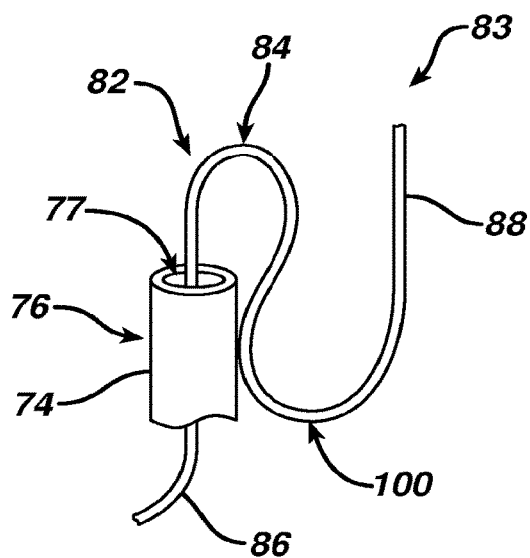
FIGS. 7-9 are schematic views of one technique for forming the slip knot shown in FIGS. 2-6.
Figure 8:
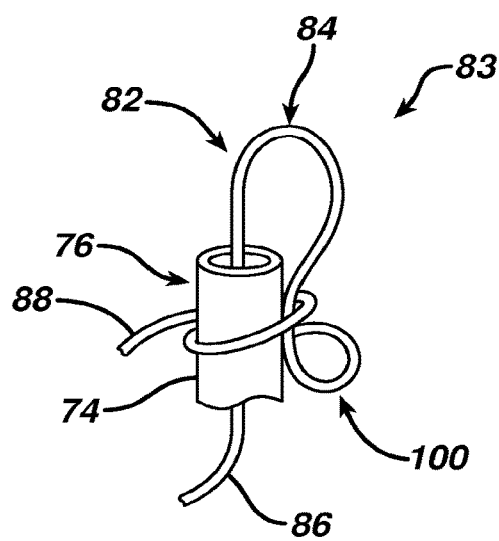
Figure 9:
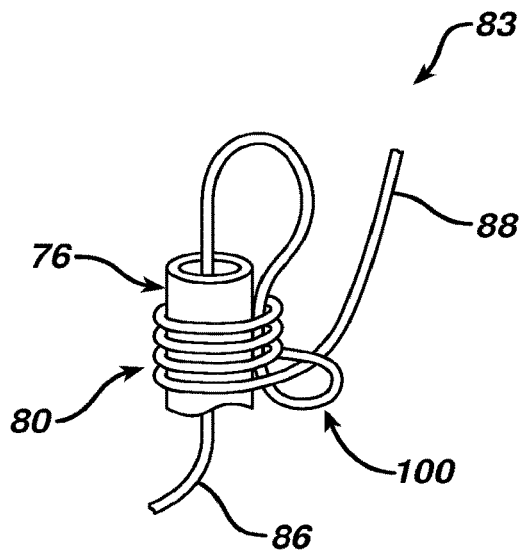

One technique for constructing filament assembly 83 is depicted in FIGS. 7-9. First filament 82 is passed through passageway 77 and a portion of tightening limb 88 is brought against the outer surface of tubular structure 74 of knot patency element 76 to form capture loop 84 and knot loop 100, FIG. 7. Tightening limb 88 is then wrapped a plurality of times, preferably two to four complete turns, around tubular structure 74, FIGS. 8 and 9, and then is passed through knot loop 100 as shown in FIG. 9. Slip knot 80 is secured in place by applying appropriate tension on tightening limb 88. In another manufacturing technique, slip knot 80 is pre-tied external to a suture anchor and then embedded in the anchor to achieve the placement and configuration shown in FIG. 9.

Figure 10:
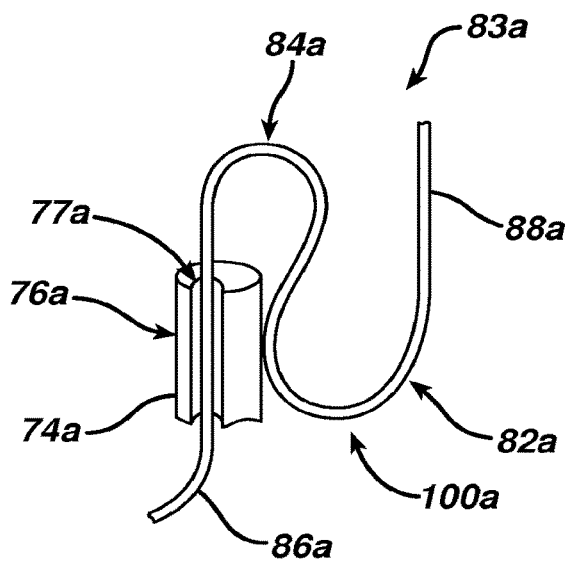
FIG. 10 is a view similar to FIG. 7 illustrating an alternative knot patency element.

Alternative knot patency elements according to the present invention have one or more channels formed as slots or other features to enable a shortening limb to pass through a sliding knot removably held by a knot patency element. For example, surgical filament assembly 83a, FIG. 10, has a tubular structure 74a of knot patency element 76a defining a slot 77a to enable shortening limb 86a of filament 82a to slide along slot 77a to reduce the size of capture loop 84a after a sliding knot (not shown) is tied through knot loop 100a but not fully tightened.

Figure 11:
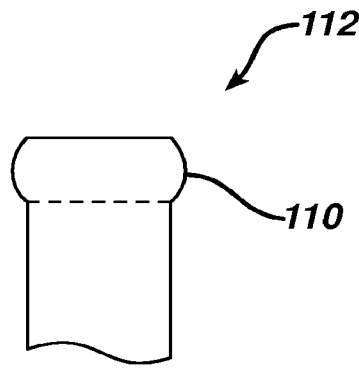
FIGS. 11-14 are side views of the proximal portion of yet other alternative knot patency elements.
Figure 12:
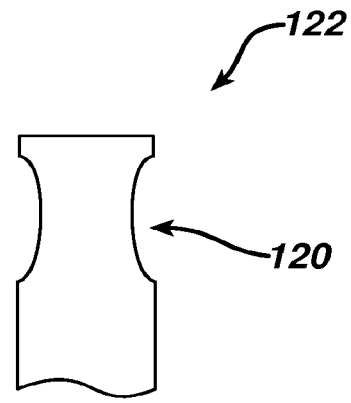
Figure 13:
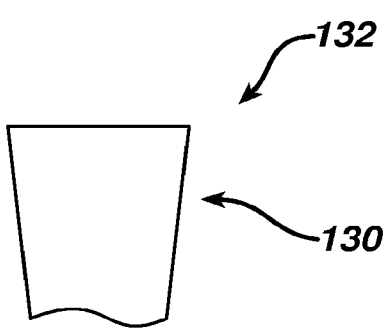
Figure 14:
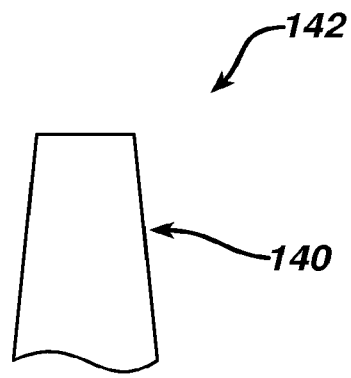

The outer geometry or surface of the knot patency elements can be modified to have one or more features that alter the tendency of a slip knot to reside on the knot patency element, such as one or more ribs or projections 110 for knot patency element 112, FIG. 11, or one or more depressions or indentations 120 for knot patency element 122, FIG. 12. The projections 110 and indentations 120 may serve as features assisting retention of a slip knot about the corresponding structure, whether tubular or other geometry, until deployment is desired. Alternatively or in addition to such discrete knot retention features, the outer surface of the knot patency element can be tapered as shown for surface 130, FIG. 13, such as frusto-conically in increasing diameter proximally if knot patency element 132 has a tubular structure, or with one or more facets increasing in width proximally if knot patency element 132 has a geometry other than cylindrical. Similarly, to enhance removal of a slip knot, a proximally-tapered surface 140, FIG. 14, can be utilized as shown for knot patency element 142. The coefficient of friction can be increased as desired, such as by texturing, or decreased as desired by providing a smooth surface. The coefficient of friction is altered in other constructions utilizing a medical-grade coating. Further, at least some of the structure of the knot patency element can be collapsible, when sufficient tension is applied to a tightening limb, to assist release of the slip knot.

Figure 15:
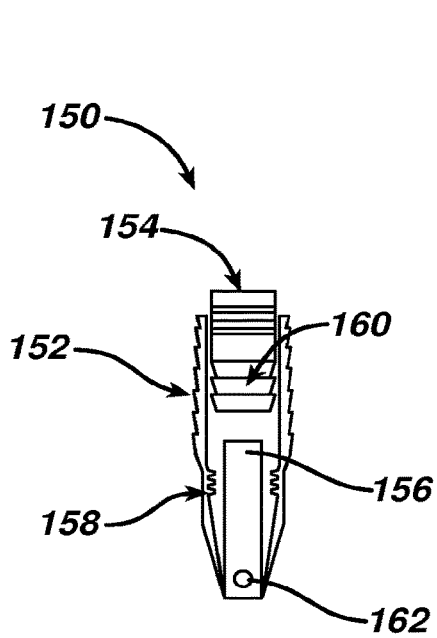
FIG. 15 is a schematic side partial cross-sectional view of yet another suture anchor according to the present invention having an internal movable locking element.

An alternative multi-part suture anchor 150 according to the present invention is shown in FIG. 15 having anchor body 152, a locking mechanism 154, and a knot patency element 156. In one construction, anchor body 152 and locking mechanism 154 are similar to the VERSALOK suture anchor system commercially available from DePuy Mitek, Raynham, Mass. Anchor body 152 has alternating teeth-like projections and indentations 158 which lockably engage ribs 160 on mechanism 154 when mechanism 154 is pushed distally into anchor body 152.

Figure 16:
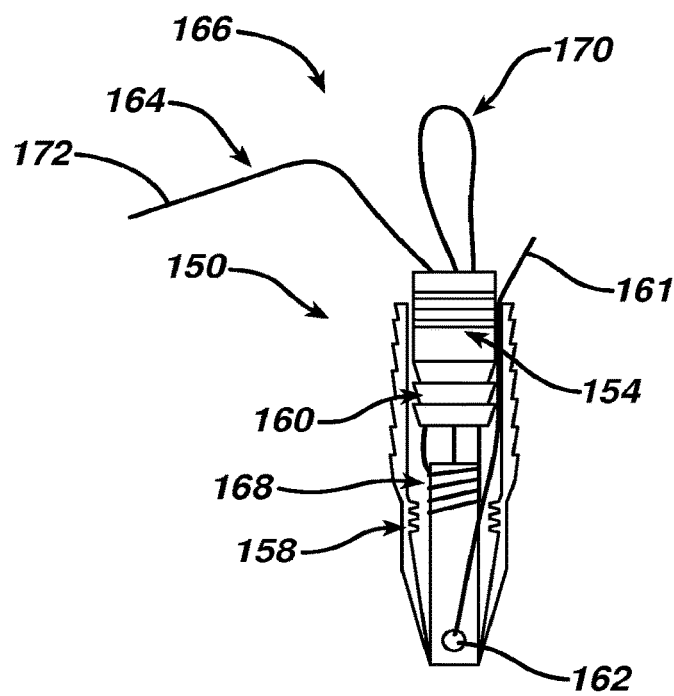
FIG. 16 is a view similar to FIG. 15 with a first filament positioned to form another surgical filament assembly according to the present invention.

Knot patency element 156 has an internal channel terminating distally in a hole 162 through which a shortening limb 161 of filament 164 is passed as shown in FIG. 16 for surgical filament assembly 166 according to the present invention. Sliding knot 168 is formed on or placed about knot patency element 156 as described above. Capture loop 170 and tightening limb 172 are directed proximally through mechanism 154. In the configuration and position shown in FIG. 16, shortening limb 161 can be manipulated to shorten capture loop 170. Once a desired size and position of capture loop 170 has been achieved, before or after an object is placed through or into capture loop 170 as desired, mechanism 154 is advanced distally to interlock with teeth 158, thereby locking shortening limb 161 into a fixed position. Final tightening of capture loop 170 to strangulate the object is accomplished by applying force to tightening limb 172.

Figure 17:
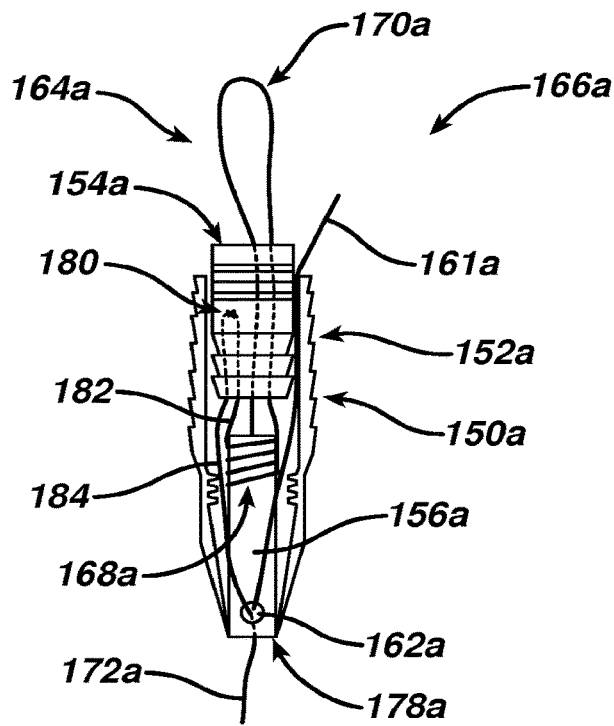
FIG. 17 is a view similar to FIG. 16 of yet another surgical filament assembly according to the present invention.

Yet another surgical filament assembly 166a according to the present invention is shown in FIG. 17, using reference numerals similar to FIG. 16 for corresponding features, which can enable one or both of a tightening limb 172a and a shortening limb 161a to extend distally beyond distal tip 178a of anchor 150a. As illustrated in FIG. 17, tightening limb 172a initially extends proximally as a first segment 182 until it passes over a bridge or post 180 and then extends distally within anchor 150a as segment 184, emerging beyond distal tip 178a as a user-accessible tightening limb 172a.

Such a distal-extending configuration may be useful in certain procedures such as an "outside-in" approach to femoral fixation of an anterior cruciate ligament for knee repair, with shortening limb 161a also extending distally or, as shown in FIG. 17, passing through hole 162a and extending proximally similar to limb 161 of FIG. 16. Another benefit of this configuration for tightening limb 172a, if post 180 is carried by mechanism 154a, is that tension applied to tightening limb 172a may provide some or all of the force to lockably engage mechanism 154 with anchor body 152a, as long as such engagement force is less than the force required to pull sliding knot 168a away from knot patency element 156a.

Alternative sliding knots include surgeon slidable knots with higher load capacity such as the Tennessee Slider described in the Arthroscopic Knot Tying Manual (2005) available from DePuy Mitek, as well as the slidable, lockable knot by Wenstrom, Jr. in U.S. Pat. No. 6,767,037, and other sliding knots which can be positioned about a knot patency element of a suture anchor according to the present invention.

Preferred materials for filaments 42 and 82, as well as for object 90, include various surgical sutures, typically size 0 to size 5, such as Orthocord™ suture commercially available from DePuy Mitek, and Ethibond™ suture available from Ethicon. Orthocord™ suture is approximately fifty-five to sixty-five percent PDS™ polydioxanone, which is bioabsorbable, and the remaining percent ultra high molecular weight polyethylene, while Ethibond™ suture is primarily high strength polyester. The amount and type of bioabsorbable material, if any, utilized in the first or second filament is primarily a matter of surgeon preference for the particular surgical procedure to be performed. In some constructions, the tightening limb and the shortening limb have different colors, sizes and/or textures to assist a surgeon or other user in selecting the appropriate limb to manipulate as desired.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A suture anchor, comprising:
    an anchor body having a distal end, a proximal end, and a longitudinal bore extending from the proximal end and towards the distal end, the anchor body having a length defined between the proximal and distal ends;
    a channel defined within the anchor body by one or more inner walls disposed within the longitudinal bore of the anchor body, a length of the channel being defined between a proximal end and a distal end thereof, the length of the channel being less than the length of the anchor body; and
    a suture construct in contact with and coupled to the one or more inner walls disposed within the longitudinal bore of the anchor body, the suture construct comprising a length of suture having a knot, the knot being disposed at a location proximal to the distal end of the channel,
    wherein the suture construct includes a collapsing loop formed through the knot, the collapsing loop having a shortening limb passing through the knot, the shortening limb being slidable through the knot when the knot is in a first uncinched configuration, and when the knot is a second cinched configuration, sliding of the shortening limb through the knot is inhibited by the knot.

2. A suture anchor according to claim 1 and further comprising a tissue suture received through the collapsing loop, the tissue suture being receivable through a tissue whereby the tissue is attachable to the anchor via the tissue suture.

3. A suture anchor according to claim 1 wherein the one or more inner walls are part of a tube having a tube cannulation extending therethrough.

4. A suture anchor, comprising:
    an anchor body having a distal end, a proximal end, and a longitudinal bore extending from the proximal end and towards the distal end, the anchor body having a length defined between the proximal and distal ends;
    a channel defined within the anchor body by one or more inner walls disposed within the longitudinal bore of the anchor body, a length of the channel being defined between a proximal end and a distal end thereof, the length of the channel being less than the length of the anchor body; and
    a suture construct in contact with and coupled to the one or more inner walls disposed within the longitudinal bore of the anchor body, the suture construct comprising a length of suture having a knot, the knot being disposed at a location proximal to the distal end of the channel, the one or more inner walls being part of a tube having a tube cannulation extending therethrough,
    wherein the suture construct includes a collapsing loop formed through the knot, the collapsing loop having a shortening limb passing through the knot, the shortening limb being slidable through the tube cannulation and through the knot when the knot is in a first non-cinched configuration to collapse the collapsible loop, and when the knot is in a second cinched configuration, sliding of the shortening limb through the knot is inhibited by the knot.

5. A suture anchor according to claim 4 and further comprising a tissue suture received through the collapsing loop, the tissue suture being receivable through a tissue whereby the tissue is attachable to the anchor via the tissue suture.

6. A suture anchor, comprising:
    an anchor body having a distal end, a proximal end, and a longitudinal axis extending from the distal end to the proximal end;
    a knot patency element disposed within a passage defined by the anchor body, the knot patency element having a central longitudinal axis that extends a length thereof, substantially parallel to the longitudinal axis of the anchor body; and
    a suture construct coupled to the anchor body, the suture construct comprising a length of suture wrapped transversely with respect to the longitudinal axis of the anchor body around the knot patency element a plurality of times such that the suture construct wraps around the knot patency element in a first plane that is generally transverse with respect to a second plane in which the longitudinal axis of the anchor body is disposed,
    wherein the knot patency element is configured to hold a knot of the suture construct in a first non-cinched configuration, the knot having a second cinched configuration.

7. A suture anchor according to claim 6 wherein the suture construct further comprises a collapsing loop formed through the knot.

8. A suture anchor according to claim 7 wherein the collapsing loop comprises a shortening limb passing through the knot, the shortening limb being slidable through the knot when the knot is in the non-cinched configuration, and when the knot is in the cinched configuration, sliding of the shortening limb through the knot is inhibited by the knot.

9. A suture anchor according to claim 7 and further comprising a tissue suture received through the collapsing loop, the tissue suture being receivable through a tissue whereby the tissue is attachable to the anchor via the tissue suture.

10. A suture anchor according to claim 6 wherein the knot patency element comprises a tube received within the knot and a tube cannulation through the tube.

11. A suture anchor according to claim 10 wherein the suture construct further comprises a collapsing loop formed through the knot and the collapsing loop comprises a shortening limb passing through the knot, the shortening limb being slidable through the tube cannulation and through the knot when the knot is in the non-cinched configuration to collapse the collapsible loop, and when the knot is in the cinched configuration, sliding of the shortening limb through the knot is inhibited by the knot.

12. A suture anchor according to claim 11 wherein the anchor body comprises a body cannulation therethrough from the proximal end to the distal end and wherein the tube is disposed within the body cannulation.

\* \* \* \* \*

UNITED STATES PATENT AND TRADEMARK OFFICE
CERTIFICATE OF CORRECTION

PATENT NO. : 10,751,041 B2
APPLICATION NO. : 15/840106
DATED : August 25, 2020
INVENTOR(S) : David B. Spenciner et al.

Page 1 of 1

It is certified that error appears in the above-identified patent and that said Letters Patent is hereby corrected as shown below:

In the Claims

Column 9, Line 53, Claim 1, change "is a second" to is in a second.

Signed and Sealed this
Twenty-ninth Day of December, 2020

Andrei Iancu
*Director of the United States Patent and Trademark Office*